United States Patent
McCord et al.

(10) Patent No.: US 9,702,006 B1
(45) Date of Patent: Jul. 11, 2017

(54) MATERIALS AND METHODS FOR DETECTING VAGINAL EPITHELIAL CELLS

(71) Applicants: Bruce McCord, Miami, FL (US); Joana Antunes, Miami, FL (US)

(72) Inventors: Bruce McCord, Miami, FL (US); Joana Antunes, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/392,824

(22) Filed: Dec. 28, 2016

(51) Int. Cl.
 *C07H 21/04* (2006.01)
 *C12Q 1/68* (2006.01)

(52) U.S. Cl.
 CPC ..... *C12Q 1/6881* (2013.01); *C12Q 2600/154* (2013.01)

(58) Field of Classification Search
 None
 See application file for complete search history.

(56) References Cited

PUBLICATIONS

Antunes et al. (Electrophoresis, vol. 37, pp. 2751, 2758, 2016).*
An, J.H. et al., "Body fluid identification in forensics," *BMB Reports*, 45:545-553.
Antunes, J. et al., "High-resolution melt analysis of DNA methylation to discriminate semen in biological stains." *Anal. Biochem.*, 2016, 494:40-45.
Antunes, J. et al., "Tissue-Specific DNA Methylation Patterns in Forensic Samples Detected by Pyrosequencing®." *Methods in Molecular Biology*, 2015, 128(1):Abstract.
Boyd-Kirkup, J.D. et al., "Epigenomics and the regulation of aging." *Epigenomics*, Apr. 2013, 5(2): 205-227, doi:10.2217/epi.13.5.
Choi, A. et al., "Body fluid identification by integrated analysis of DNA methylation and body fluid-specific microbial DNA." *Int. J. Legal Med.*, Jan. 2014, 128(1):Abstract, doi:10.1007/s00414-013-0918-4.
Eads, C.A. et al., "Combined Bisulfite Restriction Analysis (COBRA)." *Methods Mol. Biol.*, 2002, 200:Abstract.
Ehrich, M. et al., "Quantitative high-throughput analysis of DNA methylation patterns by base-specific cleavage and mass spectrometry." *PNAS*, Nov. 2005, 102:15785-90.
Frumkin, D. et al., "DNA methylation-based forensic tissue identification." *Forensic Science International: Genetics*, 2011, 5:517-524.
Hanson, E.K. et al., "Rapid and inexpensive body fluid identification by RNA profiling-based multiplex High Resolution Melt (HRM) analysis." *F1000Research*, May 2015, 2(281):1-23.
Juusola, J., Ballantyne, J., "mRNA Profiling for Body Fluid Identification by Multiplex Quantitative RT-PCR*." *J Forensic Sci*, Nov. 2007, 52(6):1252-1262.
Lee, H.Y. et al., "Potential forensic application of DNA methylation profiling to body fluid identification." *Int. J. Legal Med.*; Jan. 2012, 126(1):ABSTRACT.
Lindenbergh, A. et al., "A multiplex (m)RNA-profiling system for the forensic identification of body fluids and contact traces." *Forensic Science International:Genetics*, 2012, 6:565-577.
Madi, T. et al., "The determination of tissue-specific DNA methylation patterns in forensic biofluids using bisulfate modification and pyrosequencing." *Electrophoresis*, Jul. 2012, 33(12):Abstract.
Park, J. et al., "Identification of body fluid-specific DNA methylation markers for use in forensic science." *Forensic Science International: Genetics*, 2014, 13:147-153.
Paul, C.L., Clark, S.J., "Cytosine Methylation: Quantitation by Automated Genomic Sequencing and Genescan™ Analysis." *BioTechniques*, Jul. 1996, 21:126-133.
Tost, J., Gut, I.G., "Analysis of Gene-Specific DNA Methylation Patterns by Pyrosequencing® Technology." *Methods in Molecular Biology*, Feb. 2007, 373:89-102, doi:10.1385/1-59745-377-3:89.
Wang, Z. et al., "Screening and confirmation of microRNA markers for forensic body fluid identification." *Forensic Science International:Genetics*, 2013, 7:116-123.
Warnecke, P.M. et al., "Identification and resolution of artifacts in bisulfite sequencing." *Methods*, Apr. 27, 2002: 101-107.
Xiong, Z., Caird, P., "COBRA: a sensitive and quantitative DNA methylation assay." *Nucleic Acids Research*, Apr. 1997, 25(12):2532-2534.

* cited by examiner

*Primary Examiner* — Jeanine A Goldberg
(74) *Attorney, Agent, or Firm* — Saliwanchik, Lloyd & Eisenschenk

(57) ABSTRACT

The subject invention pertains to biomarkers for detecting vaginal epithelial cells in a sample, particularly, a forensic sample. In one embodiment, the level of methylation at the PFN3A locus in the genetic material isolated from the sample is used to detect and/or quantify vaginal epithelial cells in a sample. In another embodiment, the level of methylation at the PFN3A locus in the genetic material isolated from a sample is determined by pyrosequencing technique using specific primers described herein. A further embodiment of the invention provides a method of determining the level of methylation at the PFN3A locus in the genetic material isolated from a cell suspected of being a vaginal epithelial cell and that is isolated from a sample. Kits containing primers and reagents for carrying out the methods disclosed herein are also provided.

12 Claims, 8 Drawing Sheets

MATERIALS AND METHODS FOR DETECTING VAGINAL EPITHELIAL CELLS

GOVERNMENT SUPPORT

This invention was made with government support under 2012-DN-BX-K018 awarded by National Institute of Justice. The government has certain rights in the invention.

The Sequence Listing for this application is labeled "SeqList-22Dec16-ST25.txt", which was created on Dec. 22, 2016, and is 4 KB. The entire content is incorporated herein by reference in its entirety.

BACKGROUND OF THE INVENTION

The current methods used in forensic sciences for detecting vaginal epithelial cells in forensic samples are time consuming and presumptive. These methods are based on histological staining of glycogen-rich cells as vaginal cells. Typically a sample collected from a crime scene is used for DNA extraction and a separate portion of the sample is used for serology. Histological staining requires that cells collected from the crime scene are fixed to a microscopic slide, stained, dried, and analyzed by a microscopy expert. Moreover, the cells undergoing histological analysis are no longer viable to be used in other methods, for example, DNA extraction and analysis.

Further, the currently used methods based on histological staining of cells are prone to false results. For example, false negatives occur because the glycogen content of vaginal cells varies depending on the menstrual cycle and reproductive age. False positives can occur due the fact that buccal and urogenital skin cells (even from males) can have high content in glycogen and get stained.

Other methods currently used rely on the quantification of certain RNAs as a product of cell-specific gene expression. Gene expression at the transcription level is quantifiable by the levels of messenger RNA (mRNA) present in a specific type of cells or at the post-transcription level that occurs through micro RNA (miRNA) presence in specific tissues. Certain methods practiced to quantify mRNA or miRNA are capillary electrophoresis and high-resolution melt analysis. The use of RNA requires normalization of transcript levels with those of a housekeeping gene in the same sample. Often the normalization has to be performed by quantifying RNA levels prior to cDNA synthesis. Also, these methods do not discriminate between human and bacterial RNA, which is commonly present in most samples. Since most transcripts are present at a basal level in body fluids, the quantification of RNA for body fluid identification relies on levels of specific transcripts being higher than a certain threshold in specific cells. Lack of an accurate quantification of RNA in the sample leads to false results since it influences the threshold for the target transcript.

BRIEF SUMMARY OF THE INVENTION

The subject invention provides materials and methods for detecting vaginal epithelial cells in a sample comprising cells and/or body fluids, for example, a forensic sample.

In one embodiment, the level of methylation at the PFN3A locus in the genetic material isolated from the sample is used to detect and/or quantify vaginal epithelial cells in a sample. In another embodiment, the level of methylation at the PFN3A locus in the genetic material isolated from a sample is determined by pyrosequencing using specific primers described herein.

A further embodiment of the invention provides a method for determining the level of methylation at the PFN3A locus in the genetic material isolated from a cell, for example, a cell suspected to be a vaginal epithelial cell that is isolated from a forensic sample.

Kits containing primers and reagents for carrying out the methods disclosed herein are also provided.

Assays for determining the level of methylation at the PFN3A locus in the genetic material isolated from a sample are also provided. In certain embodiments, the assays comprise pyrosequencing using specific primers described herein.

BRIEF DESCRIPTION OF SEQUENCES

Figure 1:
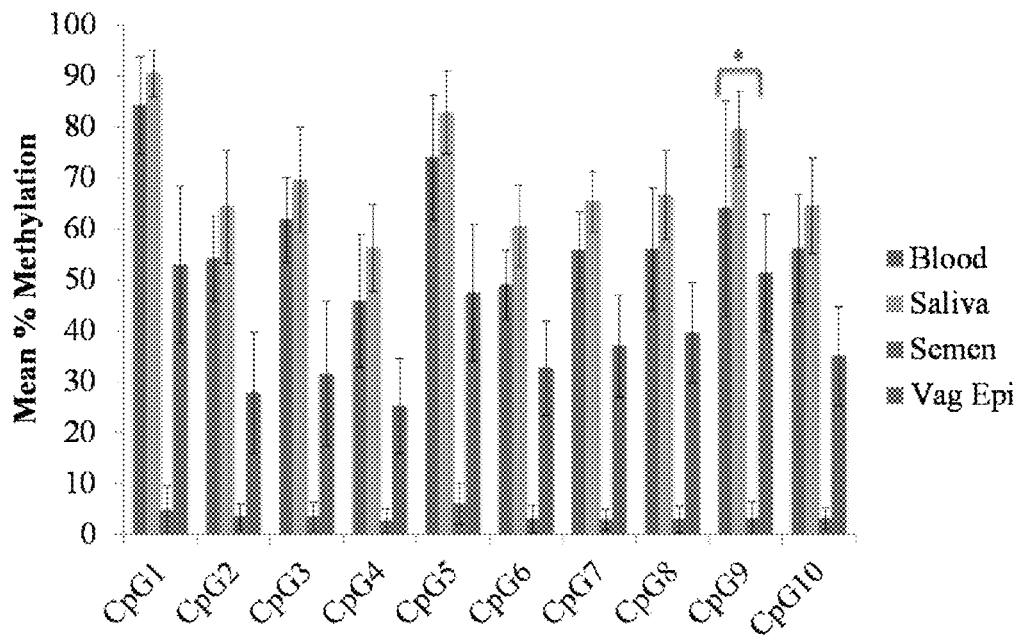
FIG. 1 provides a graph showing mean percent of methylation for samples of blood (n=8), saliva (n=11), semen (n=12) and vaginal epithelia (n=10) with 50 ng input to bisulfite. * indicates CpG positions where the difference in methylation levels is not statistically significant (p<0.05) between vaginal epithelia and blood. For each CpG position indicated on the x-axis, the bars from left to right correspond to blood, saliva, semen, and vaginal epithelial cell samples.

SEQ ID NO: 1: Sequence of PFN3 gene.
SEQ ID NO: 2: Sequence of the PFN3A locus.
SEQ ID NO: 3: Sequence of a forward primer designed to amplify the PFN3A locus.
SEQ ID NO: 4: Sequence of a reverse primer designed to amplify the PFN3A locus.
SEQ ID NO: 5: Sequence of a sequencing primer designed to sequence the PFN3A locus.
SEQ ID NO: 6: Sequence of PFN3 gene after bisulfite treatment assuming 100% methylation of all CpG sites.
SEQ ID NO: 7: Sequence of PFN3A locus after bisulfite treatment assuming 100% methylation of all CpG sites.
SEQ ID NO: 8: Example of a sequence analyzed by pyrosequencing using primer of SEQ ID NO: 5.

DETAILED DESCRIPTION OF THE INVENTION

The invention provides methods that avoid the problems and difficulties with current methods of detecting vaginal epithelial cells in a sample, particularly, a forensic sample. The methods of the invention depend on the analysis of methylation levels at a specific genetic locus, namely, the PFN3A locus, to detect vaginal epithelial cells in a sample. The sample may be, for example, a sample of body fluids.

DNA methylation is one of the epigenetic mechanisms for gene regulation. Different levels of DNA methylation in certain loci control gene expression by silencing or activating specific genes. The presence of a methyl group on the 5' carbon of a cytosine belonging to the dinucleotide CG (CpG) is believed to prevent the binding of the transcription machinery in the promoter of a gene. Some loci on the genome called "tissue-specific differentially methylated regions" (tDMRs) can therefore be used for cell identification because they present different levels of DNA methylation depending on the cell studied. To determine the pattern of DNA methylation at a locus, the most commonly used methods include the bisulfite modification of genomic DNA that chemically converts the unmethylated cytosines to uracils but does not react with methylated cytosines. During a polymerase chain reaction (PCR) the uracils get copied as thymines and the amplicons can then be sequenced to determine the presence of a cytosine or a thymine at each specific CpG.

In accordance with the subject invention, it has been found that the DNA methylation levels at the PFN3A locus are different for vaginal epithelial cells when compared to other cells, for example, cells from blood, saliva, and semen. Another common issue in forensic samples is that mixtures of body fluids are present. In certain embodiments, the invention provides materials and methods for detecting vaginal epithelial cells in a forensic sample.

Identifying vaginal epithelial cells based on DNA methylation methods provided herein does not depend on accurate quantification of human DNA present in the sample. Through the use of specific primers for bisulfite-converted DNA, primer specific amplicons are obtained that correspond to the genomic region of interest, namely, the PFN3A locus (SEQ ID NO: 2).

Forensic samples commonly contain DNA from other species, either due to exposure to the environment or due to the presence of several bacterial species that are part of the human microbiome. For that reason a method that uses nucleic acids for body fluid discrimination must be sufficiently specific to withstand the presence of non-human DNA or RNA. The methods described herein using the locus PFN3A are specific for primates and do not amplify genomic DNA from other organisms.

As such, quantification of DNA methylation levels measured by pyrosequencing at the PFN3A locus can successfully discriminate vaginal epithelial cells from other cells, for example, buccal cells, sperm, or blood cells.

The methods described herein can be practiced with minute amounts of genomic DNA, for example, between 1 ng to 50 ng, particularly, between 5 ng to 30 ng, more particularly, at about 5 ng. Moreover, methylation levels at the PFN3A locus can be performed when mixtures of body fluids are present.

Further, the invention provides pyrosequencing methods that are specific for primates and contaminations usually present in biological samples, for example, bacterial DNA, are not detected.

One embodiment of a method of the subject invention for identifying a sample as containing or not containing a vaginal epithelial cell comprises the steps of:

(a) determining the level of methylation at PFN3A locus in:
  i) a genetic material isolated from the sample, and
  ii) optionally, a control genetic material;
(b) optionally, obtaining one or more reference values corresponding to the level of methylation at PFN3A locus; and
(c) identifying the sample as:
  i) containing the vaginal epithelial cell based on the level of methylation at PFN3A locus in the genetic material isolated from the sample, or
  ii) not containing the vaginal epithelial cell based on the level of methylation at PFN3A locus in the genetic material isolated from the sample.

Various techniques are known to a person of ordinary skill in the art to determine the level of methylation at the PFN3A locus in a genetic material. Non-limiting examples of such techniques include bisulfite conversion, digestion by restriction enzymes followed by polymerase chain reaction (Combined Bisulfite Restriction Analysis, COBRA), direct sequencing, cloning and sequencing, pyrosequencing, mass spectrometry analysis or probe/microarray based assay. Certain techniques of determining methylation at certain genomic sites are described in Eads et al., Xiong et al., Paul et al., Warnecke et al., Tost et al., and Ehrich et al., the contents of which are herein incorporated in their entirety. Additional techniques for determining the level of methylation at a genetic are known to a person of ordinary skill in the art and such techniques are within the purview of the invention.

The nucleotide coordinates for genetic loci mentioned herein correspond to University of California Santa Cruz genome browser and Assembly hg38.

PFN3 gene is located on chromosome 5 in humans, more specifically in the region between 177,400,107 and 177,400,636 nucleotides. Accordingly, the term "PFN3 gene" refers to a polynucleotide having the sequence of SEQ ID NO: 1. The "PFN3A locus" refers to the part of the PFN3 gene amplified by the primers of SEQ ID NO: 3 and 4. Accordingly, PFN3A locus refers to the sequence of SEQ ID NO: 2, with the genome coordinates of chr5:177,400,199-177,400,413.

The control sample used in the methods of the invention can be obtained from one or more of the following: a known vaginal epithelial cell or a cell other than vaginal epithelial cell known to have methylation levels at the PFN3A locus to be different from the methylation level at the PFN3A locus in a vaginal epithelial cell. Non-limiting examples of cells other than vaginal epithelial cells are a buccal cell, a blood cell, and a sperm. If the control sample is a vaginal epithelial cell, the step of identifying the sample as containing the vaginal epithelial cell is based on the level of methylation at the PFN3A locus in the genetic material isolated from the sample being similar to the level of methylation at the PFN3A locus in the control genetic material. On the other hand, the step of identifying the sample as not containing the vaginal epithelial cell is based on the level of methylation at PFN3A locus in the genetic material isolated from the sample being different from the level of methylation at the PFN3A locus in the control genetic material.

If a control sample is a cell different from a vaginal epithelial cell, the step of identifying the sample as containing the vaginal epithelial cell is based on the level of methylation at the PFN3A locus in the genetic material isolated from the sample being different from the level of methylation at the PFN3A locus in the control genetic material. On the other hand, the step of identifying the sample as not containing the vaginal epithelial cell is based on the level of methylation at the PFN3A locus in the genetic material isolated from the sample being similar to the level of methylation at the PFN3A locus in the control genetic material.

The reference value corresponding to the level of methylation at the PFN3A locus can indicate the level of methylation at the PFN3A locus in a vaginal epithelial cell or a cell other than a vaginal epithelial cell. As such, the reference value corresponding to level of methylation at the PFN3A locus can indicate the presence of absence of a vaginal epithelial cell.

In one embodiment, the step of determining the level of methylation at the PFN3A locus comprises pyrosequencing. Pyrosequencing comprises the steps of:
    (a) isolating the genetic material from the sample,
    (b) treating the isolated genetic material with bisulfite,
    (c) conducting a PCR using the bisulfite treated DNA as a template and a primer pair designed to amplify the PFN3A locus, and
    (d) analyzing the PCR amplicons produced in step (c) by pyrosequencing using a sequencing primer designed to sequence the amplicons.

A primer pair can be designed to amplify the PFN3A locus based on the sequence of human genomic DNA flanking the PFN3A locus, for example, as shown in SEQ ID NOs: 1 and 2 and the sequence of human genomic DNA at the PFN3A locus and the human genomic DNA flanking the PFN3A locus after being treated with bisulfite, as shown in SEQ ID NOs: 6 and 7.

In one embodiment, the primer pair designed to amplify the PFN3A locus comprises a forward primer comprising SEQ ID NO: 3 and a reverse primer comprising SEQ ID NO: 4. A skilled artisan can design a primer pair other than SEQ ID NOs: 3 and 4 to amplify the PFN3A locus based on the sequences of SEQ ID NOs: 1-2 and 6-7 and such embodiments are within the purview of the invention.

In another embodiment, the sequencing primer comprises SEQ ID NO: 5. A skilled artisan can design a sequencing primer other than SEQ ID NO: 5 to sequence the PFN3A locus based on the sequences of SEQ ID NOs: 1-2 and 6-7 and such embodiments are within the purview of the invention. Alternately, a sequence primer can be designed based on an adapter introduced into the amplicon by incorporating the adapter into one of the forward or reverse primers.

An "adapter" as used herein is a sequence of about 10 to 20 nucleotides that can be introduced into an amplicon by incorporating the adapter into the primer used for the amplification of the amplicon. Once an amplicon contains an adapter sequence, a primer designed based on the sequence of the amplicon can be used to sequence the amplicon.

In certain embodiments, the methods described herein to identify a sample as containing a vaginal epithelial cell are practiced on a forensic sample to detect the presence of a vaginal epithelial cell in the forensic sample. In certain embodiments, the methods described herein are practiced on a forensic sample that is processed to separate a cell suspected to be a vaginal epithelial cell before the step of isolating the genetic material. The cell suspected to be the vaginal epithelial cell can be isolated from the rest of the sample based on the cell being rich in glycogen compared to other cells in the sample.

In certain embodiments, the invention provides a method for determining the level of methylation at the PFN3A locus in a genetic material from a cell, the method comprising the steps of:
    (a) isolating the genetic material from the cell,
    (b) treating the genetic material with bisulfite,
    (c) conducting a PCR using the bisulfite treated genetic material as a template and a primer pair designed to amplify the PFN3A locus, and
    (d) analyzing the PCR amplicons produced in step (c) by pyrosequencing using a sequencing primer designed to sequence the amplicons.

The details described above regarding the techniques for determining the level of methylation at the PFN3A locus in the genetic material in a sample; the PFN3A locus; the primer pair designed to amplify the PFN3A locus; the sequencing primer designed to sequence the amplicon produced from the PFN3A locus; and the types of samples are also applicable to the method described herein for determining the level of methylation at the PFN3A locus in a genetic material from a cell.

A further embodiment of the invention provides a kit comprising:
    (a) a primer pair designed to amplify the PFN3A locus in a bisulfite treated human genetic material, and (d) a sequencing primer designed to sequence an amplicon produced by a PCR conducted by using the primer pair and the bisulfite treated human genetic material as a template.

The details described above regarding the sequences of the primer pair designed to amplify the PFN3A locus in a bisulfite treated human genetic material and the sequencing primer designed to sequence the amplicons are applicable to the kits described herein.

In further embodiments, the kit comprises one or more reagents, for example, reagents for treating a sample, reagents for isolating cells from the sample, reagents for isolating genetic material from the sample, reagents for bisulfite treating the genetic material, reagents for conducting PCR, and reagents for conducting pyrosequencing.

As used herein, the singular forms "a," "an" and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," include the phrases "consisting essentially of," "consists essentially of," "consisting," and "consists."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

As used herein, the term "level of methylation" or "methylation status" as applied to a genetic locus refers to whether one or more cytosine residues present in a CpG have or do not have a methylation group. The level of methylation or methylation status refers to the percentage of cells in a sample that do or do not have a methylation group on such cytosines. For example, if 50 cells in a pool of 100 cells contain methylated cytosines at a CpG site, the level of methylation or methylation status of the CpG site is 50%.

Materials and Methods

Blood, buccal, vaginal swabs, and semen samples were collected from human volunteers. Swabs were air-dried and DNA extraction was performed using the EZ1® DNA Investigator kit (Qiagen, CA) and the BioRobot® EZ1 automated purification workstation (Qiagen, CA) according to the manufacturer's specifications. Quantification was performed using the PicoGreen® method (Life Technologies, CA). Fifty nanograms of genomic DNA was bisulfite modified using the EpiTect® Fast DNA Bisulfite Kit (Qiagen, CA) according to manufacturer's instructions. For the sensitivity studies, six vaginal epithelia samples were serially diluted to obtain 10, 5 and 1 ng of input DNA for bisulfite conversion. For the mixtures studies, genetic material samples of blood, vaginal epithelial cells, and semen were quantified and mixed in different ratios of each of the two body fluids to have 100 ng total of DNA input to bisulfite modification. For the species-sensitivity studies, DNA from cat, dog, chicken, cow, mice, bacterial pool (*Escherichia coli, Staphylococcus aureus, Enterococcus faecalis* and *Pseudomonas aeruginosa*), horse, gorilla, orangutan and chimpanzee was collected and processed like described above. DNA from a sample of human vaginal epithelia was used as the positive control.

DNA amplification reactions were performed using the PyroMark® PCR kit (Qiagen, CA) by adding 2 µL of bisulfite-modified DNA to each reaction and following manufacturer's instructions. Primers for amplifying the PFN3A locus are provided in Table 1. The PCR products and a low molecular weight ladder (New England Biolabs, MA) were run in 2% agarose gels, stained with ethidium bromide to confirm the presence and size of amplicons.

Pyrosequencing reactions were performed using a PyroMark® Q24 pyrosequencer (Qiagen) using 10 µL of PCR product and the protocol established by the manufacturer. The percent methylation for each individual CpG was automatically calculated by the PyroMark® Q24 software version 2.0.6 (Qiagen, CA).

Statistical analysis was performed using SPSS version 22. Methylation percent was compared between body fluids for each CpG performing a one-way ANOVA followed by Tukey-HSD post-hoc test. For the sensitivity studies, a dependent t-test was performed to compare the percent methylation of each CpG from each dilution to the 50 ng group. p-value below 0.05 represented that the difference observed is significant for all statistical tests performed.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Pyrosequencing Analysis of the PFN3A Locus

Pyrosequencing of 8-12 genetic material samples from each body fluid was performed. The results from each genetic material sample from each body fluid were displayed by the Qiagen software as a pyrogram that calculates percent of methylation for 10 individual CpGs within the PFN3A region. The percent of methylation for each CpG from each body fluid were recorded and the arithmetic average and standard deviations were calculated (FIG. 1). Statistical analysis was performed and only the CpGs that have p<0.05 between vaginal epithelia and all other body fluids are reported. The intermediate level of mean percent methylation for 9 out of 10 CpGs within the PFN3A locus from vaginal epithelial cells was significantly different when compared to the other body fluids/cells. One CpG within the PFN3A locus, namely, CpG9, presents a p-value larger than 0.05, which shows that methylation levels between blood and vaginal epithelia are very similar at CpG9.

In one embodiment, the subject invention provides a set of primers for PCR and pyrosequencing that allows quantification of DNA methylation near the PFN3A locus. Gene PFN3 is located on chromosome 5 in humans, more specifically in the region between 177,400,107 and 177,400,636. The primers were designed to amplify and analyze the genome coordinates chr5:177,400,199 to 177,400,413. The region amplified and analyzed by these primers includes 10 CpGs, particularly, the cytosines at positions 33, 36, 38, 41, 61, 63, 65, 67, 70, and 74 of SEQ ID NO: 2. The levels of DNA methylation for 9 out of these 10 CpGs were statistically different in vaginal epithelial cells when compared to blood, saliva, and semen. The primers sequence is shown in Table 1.

TABLE 1

Sequence of PFN3A primers.

| Primer | Sequence |
| --- | --- |
| Forward | 5'-GTG TAT AGT TTT GTT GAG GAT GTT TT-3' (SEQ ID NO: 3) |
| Reverse* | 5'-ACA AAC ACA CCT TCC TAC AA-3' (SEQ. ID NO: 4) |
| Sequencing | 5'-GTT TTG TTG AGG ATG TTT TT-3' (SEQ ID NO: 5) |

*indicates biotin modification of the primer

The levels of methylation for each body fluid were averaged and displayed in FIG. 1.

In one embodiment, pyrosequencing analyzes provides the sequence of SEQ ID NO: 8. The cytosines at positions 33, 36, 38, 41, 61, 63, 65, 67, 70, and 74 of SEQ ID NO: 2 correspond to positions 6, 9, 11, 14, 34, 36, 38, 40, 43, and 47 of SEQ ID NO: 8.

Example 2—Methods Require Minute Amounts of Starting DNA

Figure 2:
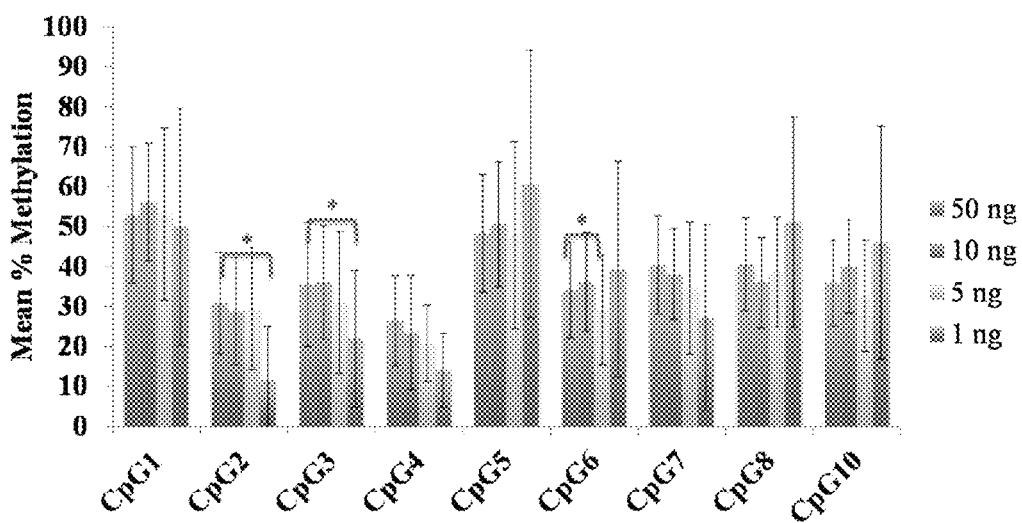
FIG. 2 provides a graph showing mean percent of methylation for vaginal epithelia samples (n=6) with different input of DNA. * indicates CpG positions and nanograms of DNA that present methylation levels with statistically significant differences (p<0.05) between groups. For each CpG position indicated on the x-axis, the bars from left to right correspond to 50 ng, 10 ng, 5 ng, and 1 ng DNA.
Figure 3:
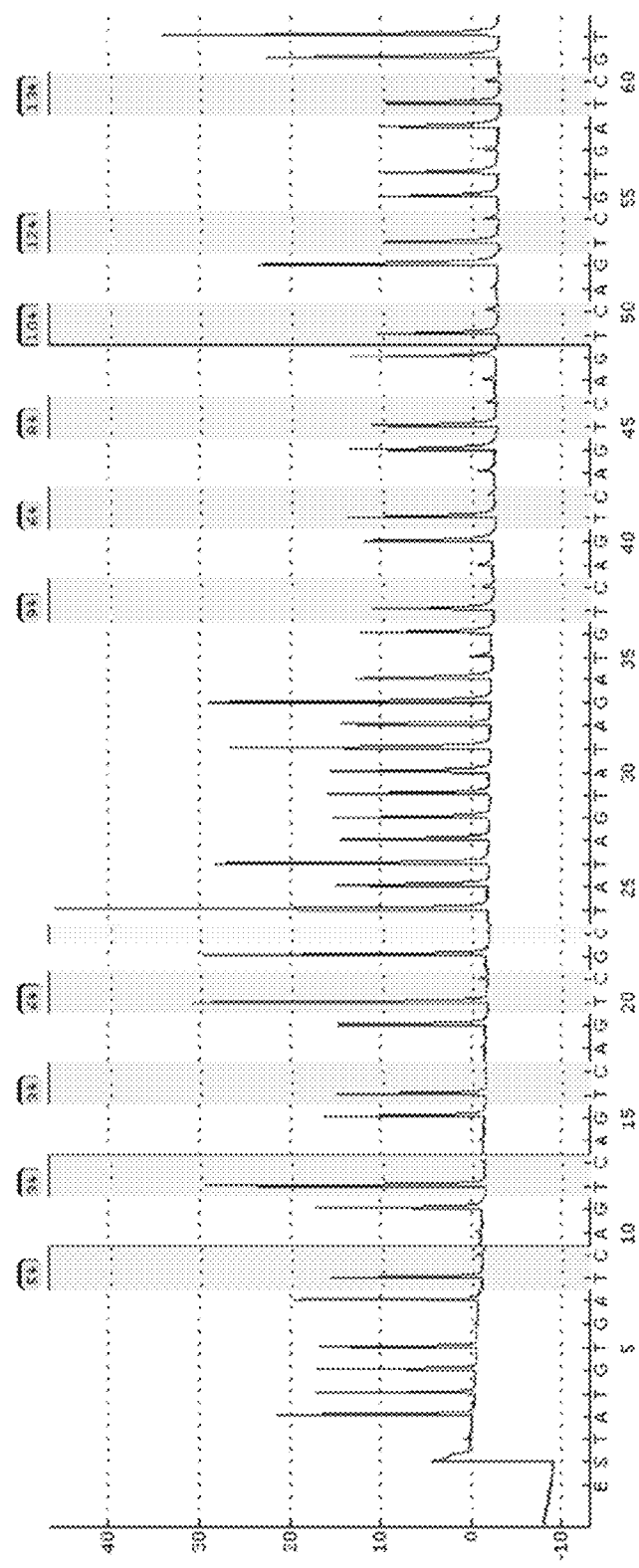
FIG. 3 provides pyrogram showing a sample with 1 ng input to bisulfite. Peak height for the majority of peaks corresponding to single nucleotide dispensations are lower than 20 light units (y-axis) which creates a warning recorded by software.

Forensic evidence often contains only a small amount of DNA, which can severely hinder the ability to obtain reliable results. To determine the sensitivity of the methods described herein, six genetic material samples of vaginal epithelial cells were quantified and diluted to add 10, 5, and 1 ng of genetic material to bisulfite conversion, followed by PCR amplification and pyrosequencing. The mean percents of methylation of the diluted samples were then compared with those of samples with 50 ng input to bisulfite conversion. Samples with 5 ng DNA indicated that only one CpG (CpG6) showed the level of methylation to be different when compared to the samples containing 50 ng DNA (FIG. 2). In the samples with 5 ng DNA, CpG2 and GpG3 showed differences in methylation levels when compared to 50 ng genetic material samples. The pyrograms generated from the samples containing 1 ng DNA indicated warnings due to low peak height (FIG. 3).

The sensitivity studies showed that data can be obtained with as little as 1 ng of DNA input to bisulfite because the methylation levels are the same as the ones presented by the 50 ng samples for 7 out of 9 CpGs. However the data show that as the input of DNA decreases the peak height in the pyrogram also decreases, which leads to warnings provided by the software.

Example 3—Analyzing Methylation Status in Samples Containing Mixtures of Cells

Figure 4:
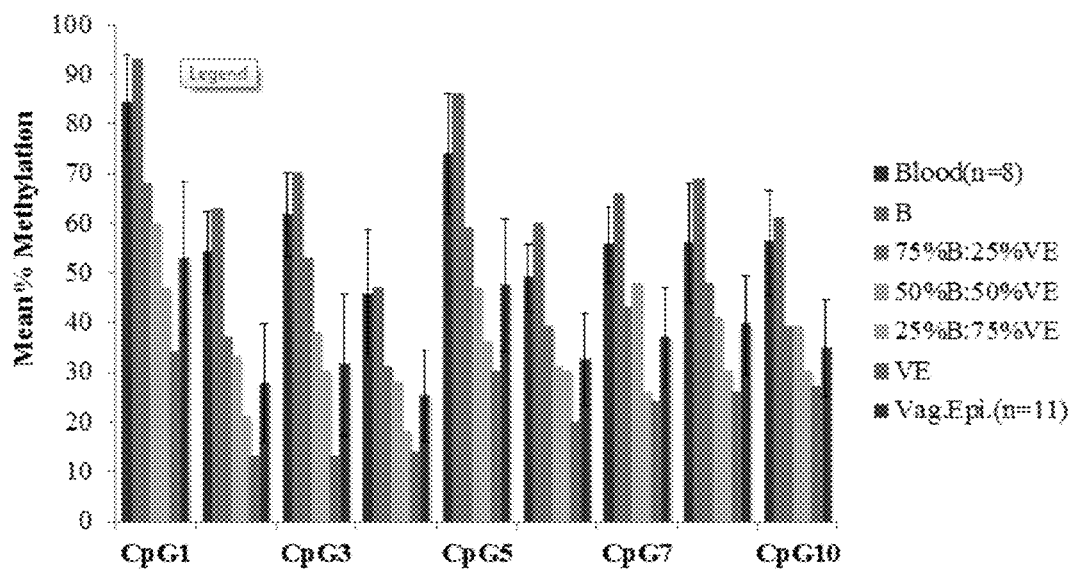
FIG. 4 provides mean percent of methylation for samples containing different ratios of DNA from blood (B) and vaginal epithelia (VE). With the decrease in the content of DNA from blood compared to vaginal epithelia, a decrease in the percent of methylation is also observed. The average percent methylation for the blood (n=8) and vaginal epithelia (n=11) samples are shown as control. The samples labeled B and VE are the DNA from blood and vaginal epithelia, respectively, used to make the mixture. For each CpG position indicated on the x-axis, the bars from left to right correspond to blood (n=8), B, 75% B:25% VE, 50% B:50% VE, 25% B:75% VE, VE, and vaginal epithelial samples (n=11).

Three randomly selected genetic material samples, one from each body fluid, were quantified for DNA methylation levels at the PFN3A locus and the methylation levels were compared to the average methylation for each body fluid (FIG. 1). The same randomly selected genetic material samples were mixed with each other in ratios of 75:25, 50:50, and 25:75 and the methylation levels at the PFN3A locus were assessed. FIG. 4 shows that samples containing mixtures of blood and vaginal epithelia have methylation values intermediate to those of samples containing only blood or vaginal epithelial cells. Moreover there is a decrease in methylation percent as the ratio of blood to vaginal epithelia decreases.

Figure 5:
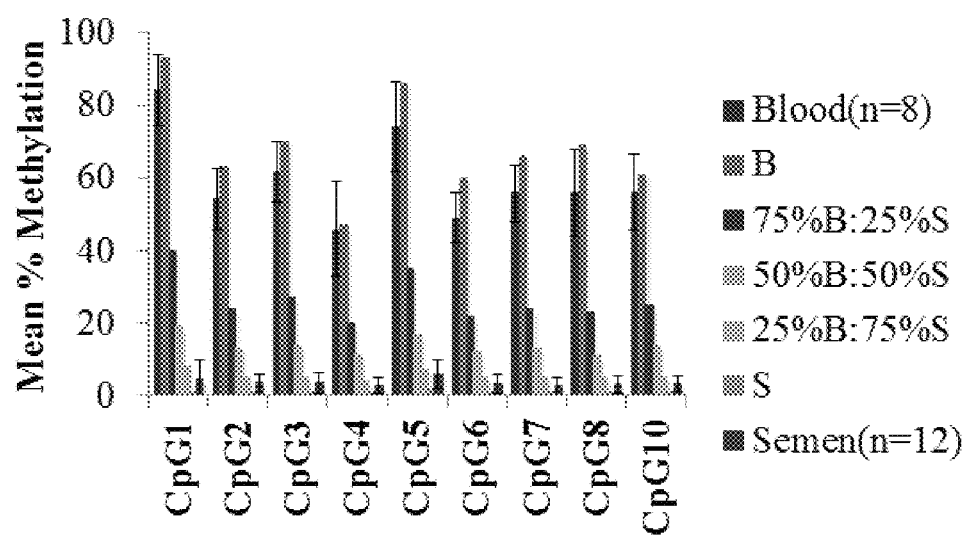
FIG. 5 provides mean percent of methylation for samples containing different ratios of DNA from blood (B) and semen (S). With the decrease in the content of DNA from blood compared to semen, a decrease in the percent of methylation is also observed. The average percent methylation for the blood (n=8) and semen (n=12) samples are shown as control. The samples labeled B and S are the DNA from blood and semen, respectively, used to make the mixture. For each CpG position indicated on the x-axis, the bars from left to right correspond to blood (n=8), B, 75% B:25% S, 50% B:50% S, 25% B:75% S, S, and semen samples (n=12).
Figure 6:
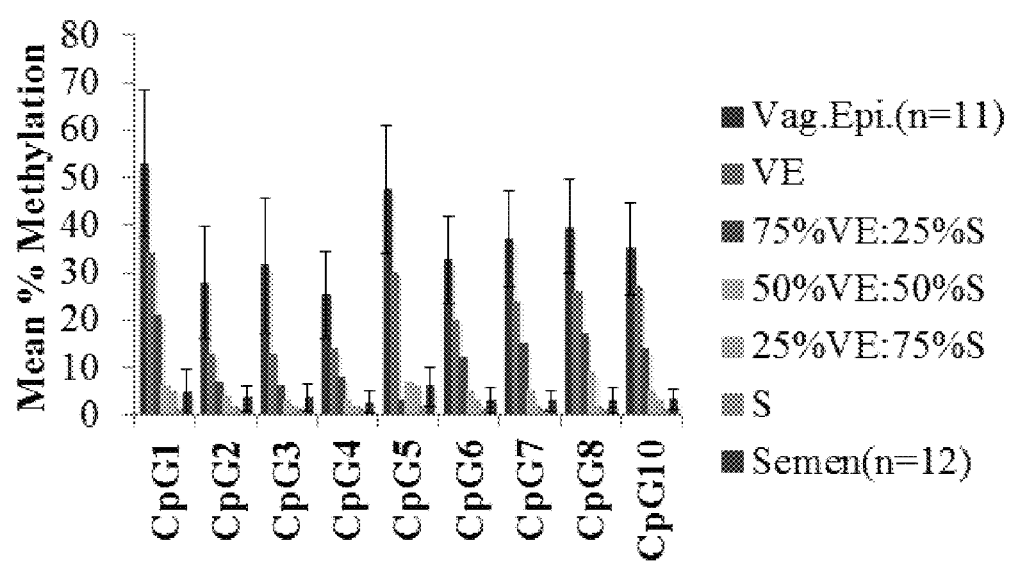
FIG. 6 provides mean percent of methylation for samples containing different ratios of DNA from vaginal epithelia (VE) and semen (S). With the decrease in the content of DNA from vaginal epithelia compared to semen, a decrease in the percent of methylation is also observed. The average percent of methylation for the vaginal epithelial cell sample (n=1) and semen (n=12) samples are shown as control. The samples labeled VE and S are the DNA from vaginal epithelia and semen, respectively, used to make the mixture. For each CpG position indicated on the x-axis, the bars from left to right correspond to vaginal epithelial cells samples (n=11), VE, 75% VE:25% S, 50% VE:50% S, 25% VE:75% S, S, and semen samples (n=12).

A similar correlation is also observed for the samples containing blood and semen (FIG. 5) as well as samples where vaginal epithelia and semen are in the mixture (FIG. 6).

FIGS. 4-6 indicate that the PFN3A locus can be used as a vaginal epithelial cell marker, for example, in forensic identification of body fluids. PFN3A locus can be used in combination with additional genetic loci capable of discriminating vaginal epithelial cells based on DNA methylation levels.

Example 4—the Methods are Specific for Primate DNA

To determine whether the methods described herein are hindered by the presence of non-human genetic material, DNAs from cat, dog, chicken, cow, mice, and bacteria (a mixture of *Escherichia coli, Staphylococcus aureus, Enterococcus* faecali and *Pseudomonas aeruginosa*), horse, gorilla, orangutan, and chimpanzee were tested. A human genetic material sample was used as a positive control. In the agarose gel analysis, only the samples from cat, cow, orangutan and gorilla showed faint bands and only the human and chimpanzee showed bright bands. All PCR products were pyrosequenced to confirm the absence of peaks in the pyrograms. The presence of bands in the agarose gel results from cat, cow, orangutan, and gorilla arise from non-specific amplification because 45 PCR cycles are necessary to amplify bisulfite-modified DNA. When pyrosequencing is performed on these samples, the sequence should not correspond to the expected sequence and the software should display red warnings.

Figure 7A:
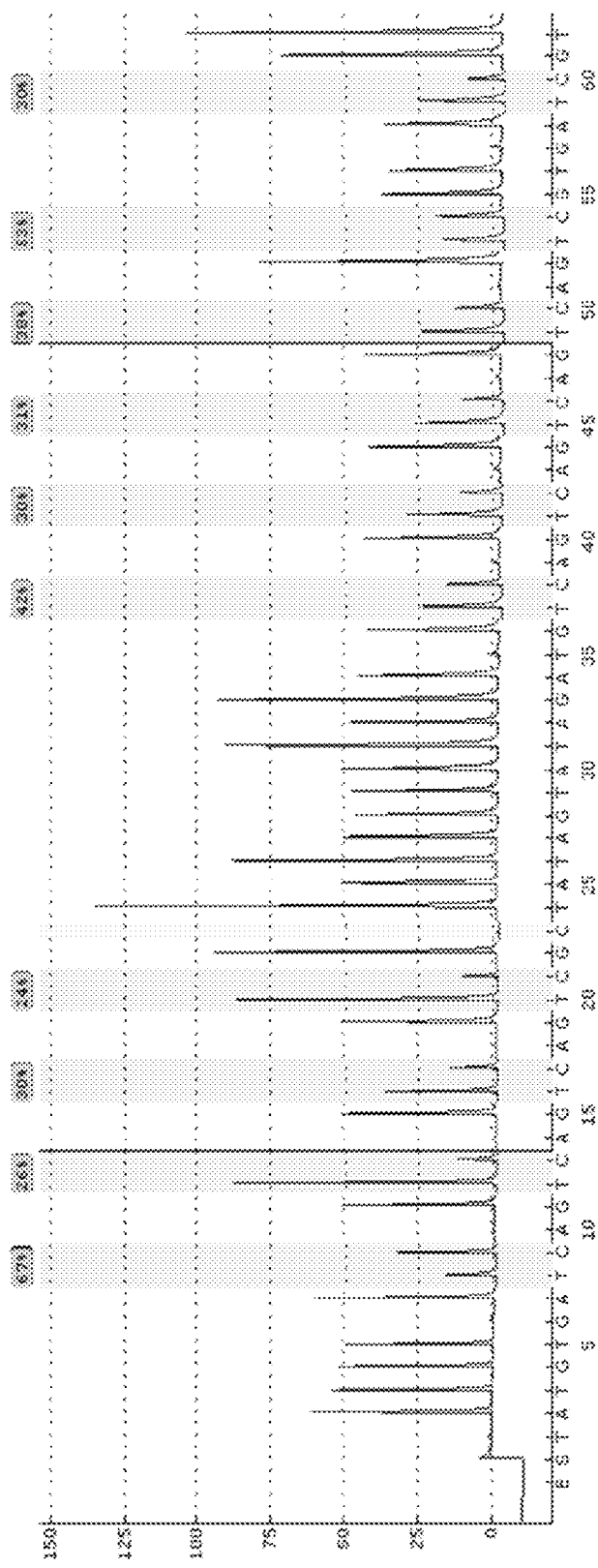
FIGS. 7A-7B show pyrograms for the PFN3A locus showing genetic material samples from (A) chimpanzee and (B) human after pyrosequencing. Both samples show good peak height and expected sequence therefore all CpGs analyzed passed the quality test imposed by the software.
Figure 7B:
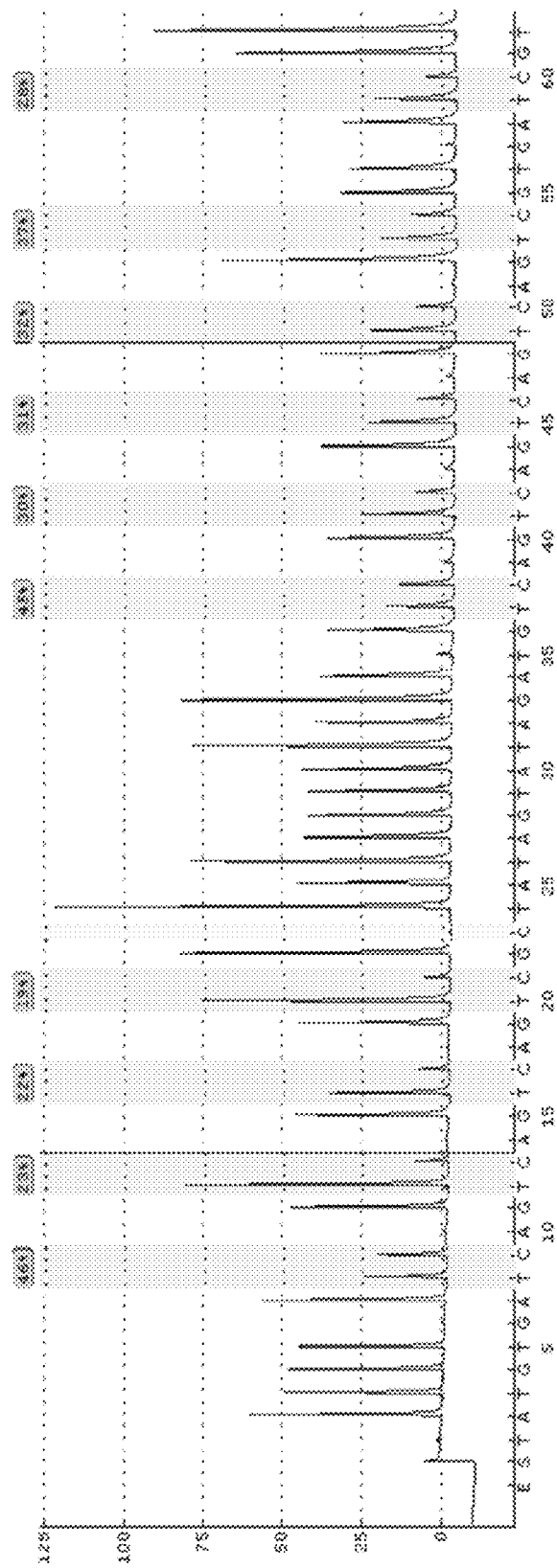
Figure 8:
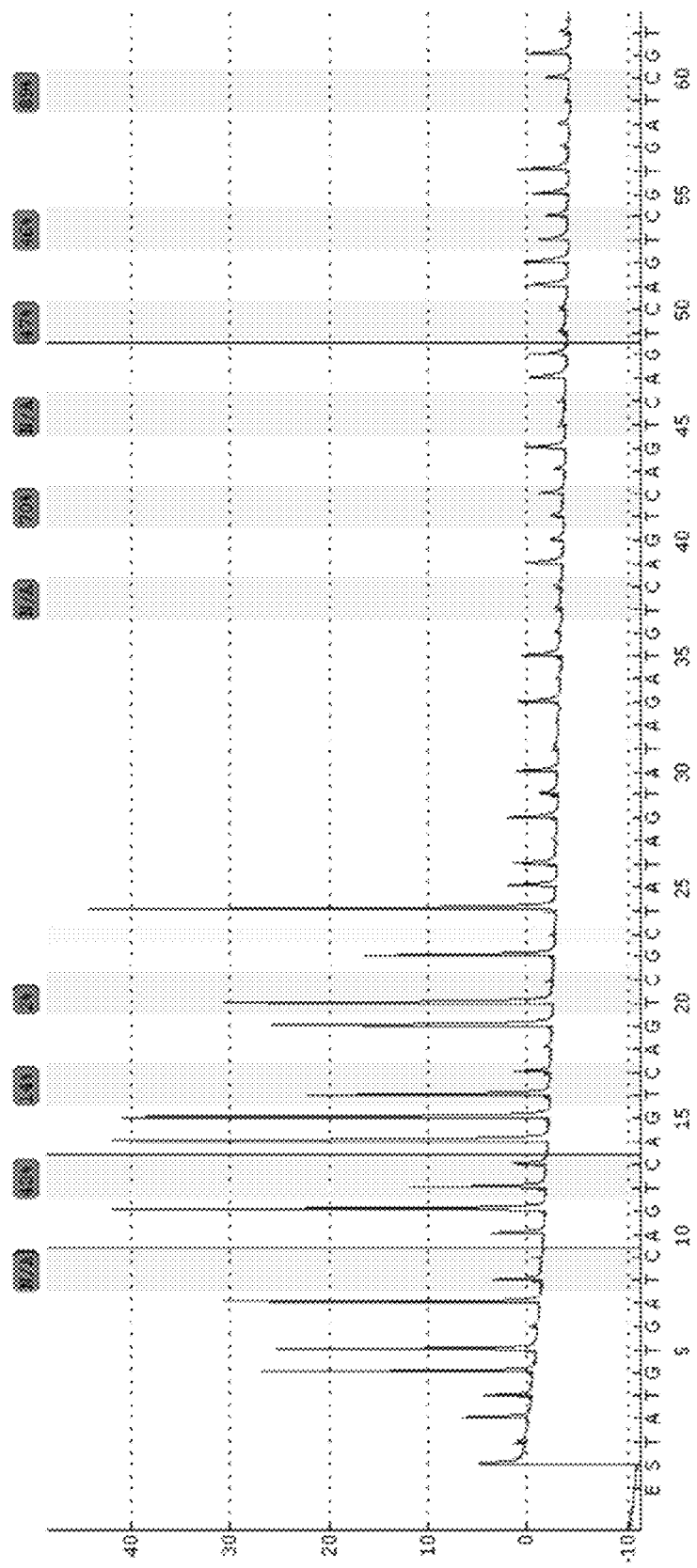
FIG. 8 shows pyrogram for the PFN3A locus showing a genetic material sample from cow as an example of how red warnings are displayed by the software when the sequence in the pyrogram does not correspond to the sequence expected.
Figure 9:
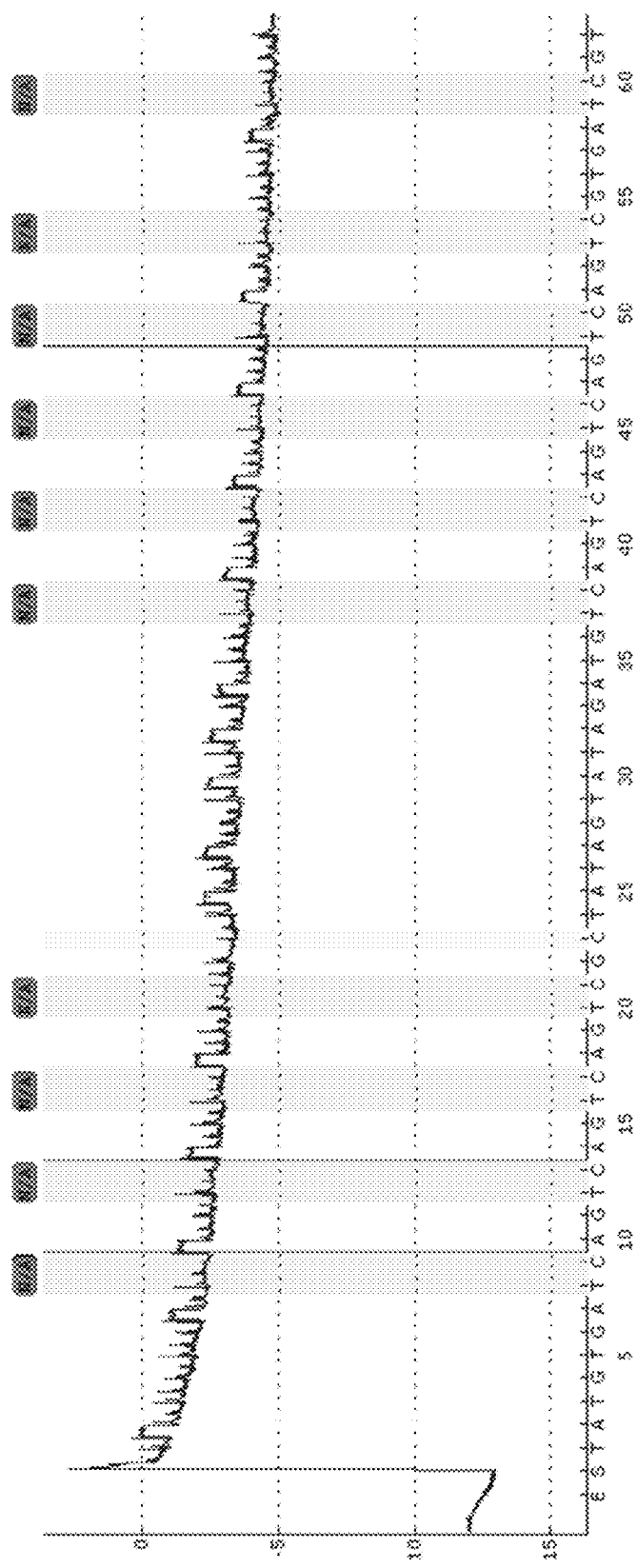
FIG. 9 shows pyrogram for the PFN3A locus showing the absence of peaks from a genetic material sample extracted from a bacterial pool containing the following species: *Escherichia coli, Staphylococcus aureus, Enterococcus faecali* and *Pseudomonas aeruginosa*. The pyrograms displayed for the genetic material samples of dog, chicken, mice and horse show absence of peaks similarly to this one.

Only the samples from human and chimpanzee present a pyrogram without warnings (FIG. 7). For the samples of cat, cow, gorilla and orangutan the pyrogram shows peaks that do not correspond to the expected DNA sequence, which indicates that the DNA sequenced is not specific for the PFN3A locus. Pyrosequencing for DNA analysis requires the user to input the sequence to analyze so that the software can automatically compare the peaks on the pyrogram with the expected peaks from the sequence to analyze. FIGS. 7B and 8 show that the observed peak height for the tested sample does not correspond to the peak height of the expected sequence. As such, the bands observed in the agarose gel are due to non-specific amplification during PCR. All other samples provided negative results with no peaks present in the pyrograms. One of those samples is the DNA from bacterial pool (FIG. 9). The absence of peaks is expected since no bands were observed in the agarose gel for these samples. These data indicate that the primers and pyrosequencing methods described herein are specific for human DNA.

REFERENCES

[1] Zubakov, D., Kayser, M., in: Primorac, D., Schnfield, M. (Ed.), *Forensic DNA applications: An Interdisciplinary Perspective*, Boca Raton, CRC Press 2014, pp. 389-390, 404.
[2] Juusola, J., Ballantyne, J. J. *Forensic Sci.* 2007, 52, 1252-1262.
[3] Wang, Z., Zhang, J., Luo, H., Ye, Y. et al. *Forensic Sci. Int.-Genet.* 2013, 7, 116-123.
[4] Lindenbergh, A., de Pagter, M., Ramdayal, G., Visser, M. et al. *Forensic Science International-Genetics* 2012, 6, 565-577.
[5] Hanson, E., Ballantyne, J. *F1000 Research* 2014, 2, 281.
[6] Boyd-Kirkup, J. D., Green, C. D., Wu, G., Wang, D., Han, J. J. *Epigenomics* 2013, 5, 205-227.
[7] An, J. H., Shin, K., Yang, W. I., Lee, H. Y. *Bmb Reports* 2012, 45, 545-553.
[8] Choi, A., Shin, K., Yang, W. I., Lee, H. Y. *Int. J. Legal Med.* 2014, 128, 33-41.
[9] Frumkin, D., Wasserstrom, A., Budowle, B., Davidson, A. *Forensic Science International-Genetics* 2011, 5, 517-524.
[10] Madi, T., Balamurugan, K., Bombardi, R., Duncan, G., McCord, B. *Electrophoresis* 2012, 33, 1736-1745.
[11] Antunes, J., Silva, D S B S., Kuppareddi, B., Duncan, G., Alho, C S., McCord, B. *Analytical Biochemistry* 2016, 494, 40-45.
[12] Antunes, J., Balamurugan, K., Duncan, G., McCord, B., in: Lehmann, U. and Tost, J. (Eds.), *Methods in Molecular Biology*, Springer New York 2015, pp. 397-409.
[13] Lee, H. Y., Park, M. J., Choi, A., An, J. H. et al. *Int. J. Legal Med.* 2012, 126, 55-62.
[14] Park, J., Kwon, O., Kim, J. H., Yoo, H. et al. *Forensic Science International-Genetics* 2014, 13, 147-153.
[15] Eads C, Laird P. Combined bisulfite restriction analysis (COBRA). Methods Mol Biol. 2002; 200:71-85.
[16] Xiong Z, Laird P. COBRA: a sensitive and quantitative DNA methylation assay. Nucleic Acids Res. 1997; 25:2532-4.
[17] Paul C, Clark S. Cytosine methylation: quantitation by automated genomic sequencing and GENESCAN analysis. Biotechniques. 1996; 21:126-33.
[18] Warnecke P, Stirzaker C, Song J, Grunau C, Melki J, Clark S. Identification and resolution of artifacts in bisulfite sequencing. Methods. 2002; 27:101-7.
[19] Tost J, Gut I. Analysis of gene-specific DNA methylation patterns by pyrosequencing technology. Methods Mol Biol. 2007; 373:89-102.
[20] Ehrich M, Nelson M, Stanssens P, Zabeau M, Liloglou T, Xinarianos G, et al. Quantitative high-throughput analysis of DNA methylation patterns by base-specific cleavage and mass spectrometry. Proc Natl Acad Sci USA. 2005; 102:15785-90.

We claim:

1. A method for identifying a sample as containing or not containing a vaginal epithelial cell, the method comprising the steps of:
   (a) determining the level of methylation at SEQ ID NO: 2 in:
      i) a genetic material isolated from the sample, and
      ii) optionally, a control genetic material;
   (b) optionally, obtaining one or more reference values corresponding to the level of methylation at SEQ ID NO: 2; and
   (c) identifying the sample as:
      i) containing the vaginal epithelial cell based on the level of methylation of the cytosines at positions 33, 36, 38, 41, 61, 63, 65, 67, and 74 of SEQ ID NO: 2 in the genetic material isolated from the sample, or
      ii) not containing the vaginal epithelial cell based on the level of methylation of the cytosines at positions 33, 36, 38, 41, 61, 63, 65, 67, and 74 of SEQ ID NO: 2 in the genetic material isolated from the sample,
   wherein the step of determining the level of methylation at SEQ ID NO: 2 comprises:
      (a) isolating the genetic material from the sample,
      (b) treating the isolated genetic material with bisulfite,
      (c) conducting a PCR using the bisulfite treated DNA as a template and a primer pair comprising a forward primer comprising SEQ ID NO: 3 and a reverse primer comprising SEQ ID NO: 4, and
      (d) analyzing the PCR amplicons produced in step (c) by pyrosequencing using a sequencing primer comprising the sequence of SEQ ID NO: 5.

2. The method of claim 1, characterized in that the control sample is obtained from one or more of the following: a known vaginal epithelial cell or a cell other than vaginal epithelial cell known to have methylation level at SEQ ID NO: 2 to be different from the methylation level at SEQ ID NO: 2 in the known vaginal epithelial cell.

3. The method of claim 2, characterized in that the cell other than vaginal epithelial cell is a buccal cell, a blood cell, or a sperm.

4. The method of claim 1, characterized in that the sample is a forensic sample.

5. The method of claim 1, characterized in that the sample is processed to separate a cell suspected to be the vaginal epithelial cell before step (a) of isolating the genetic material.

6. The method of claim 5, characterized in that the cell suspected to be the vaginal epithelial cell is isolated based on the cell being rich in glycogen compared to other cells in the sample.

7. A method for determining the level of methylation at the PFN3A locus in a genetic material from a cell, the method comprising the steps of:
   (a) isolating the genetic material from the cell,
   (b) treating the genetic material with bisulfite,
   (c) conducting a PCR using the bisulfite treated genetic material as a template and a primer pair comprising a forward primer comprising SEQ ID NO: 3 and a reverse primer comprising SEQ ID NO: 4, and
   (d) analyzing the PCR amplicons produced in step (c) by pyrosequencing using a sequencing primer comprising the sequence of SEQ ID NO: 5.

8. The method of claim 7, characterized in that the cell is isolated from a forensic sample.

9. The method of claim 8, characterized in that the cell isolated from the forensic sample is suspected to be a vaginal epithelial cell.

10. The method of claim 9, characterized in that the cell suspected to be the vaginal epithelial cell is isolated from the forensic sample based on the cell being rich in glycogen compared to other cells in the sample.

11. A kit comprising a forward primer comprising SEQ ID NO: 3 and a reverse primer comprising SEQ ID NO: 4.

12. The kit of claim 11, the kit further comprising a sequencing primer comprising SEQ ID NO: 5.

* * * * *

UNITED STATES PATENT AND TRADEMARK OFFICE
CERTIFICATE OF CORRECTION

PATENT NO.         : 9,702,006 B1
APPLICATION NO.    : 15/392824
DATED              : July 11, 2017
INVENTOR(S)        : Bruce McCord and Joana Antunes Page 1 of 1

It is certified that error appears in the above-identified patent and that said Letters Patent is hereby corrected as shown below:

In the Specification

Column 2,
Line 67, "(n=1)" should read --(n=11)--.

Signed and Sealed this
Twentieth Day of March, 2018

Andrei Iancu
*Director of the United States Patent and Trademark Office*

SEQUENCE LISTING

<160> NUMBER OF SEQ ID NOS: 8

<210> SEQ ID NO 1
<211> LENGTH: 530
<212> TYPE: DNA
<213> ORGANISM: Homo sapiens

<400> SEQUENCE: 1

```
cgcccaggtc acagtttatt tggcccgcgc taccagtggg cggcctggct ggccggctag      60
gcgccctgca tgcgcagccc gcgtatgagt tcgtgcaccg tcttgttgag gatgccccca     120
tgtacgccgc gtcggcccat tagcaccagg agcgcgcgcg gcgcacggcc cacgcacacg     180
gcgcgcgcgt ccagcccctt ggtgcgtgcg tccagcacgc cgtcaccctc ggccagcagg     240
tggtcgcgga tgacgcagca gcggcggccc cccacgctca ggcccgcctg caggaaggtg     300
tgcctgtccg gccccgtgag cacgcccacc tcctgcggcg agatggccgc cagcaggccc     360
ccgggccgcg aagcccacac gcagctgttg tccgcatggc ccacgatggc cacgtcgtcg     420
atgcgctggt cccgcagcac tgcactgatg tagaccttcc agtcgcccat cgcgctccga     480
gtgcgcccag ccgcctcgca cctctcgggg aaatatagag gcgccacgcg              530
```

<210> SEQ ID NO 2
<211> LENGTH: 215
<212> TYPE: DNA
<213> ORGANISM: Homo sapiens

<400> SEQUENCE: 2

```
gtgcaccgtc ttgttgagga tgcccccatg tacgccgcgt cggcccatta gcaccaggag      60
cgcgcgcggc gcacggccca cgcacacggc gcgcgtcc agcccttgg tgcgtgcgtc     120 cagcacgccg tcaccctcgg ccagcaggtg gtcgcggatg acgcagcagc ggcggccccc     180
```

```
cacgctcagg cccgcctgca ggaaggtgtg cctgt                                215
```

<210> SEQ ID NO 3
<211> LENGTH: 26
<212> TYPE: DNA
<213> ORGANISM: Homo sapiens

<400> SEQUENCE: 3

```
gtgtatagtt tgttgagga tgtttt                                           26
```

<210> SEQ ID NO 4
<211> LENGTH: 20
<212> TYPE: DNA
<213> ORGANISM: Homo sapiens

<400> SEQUENCE: 4

```
acaaacacac cttcctacaa                                                 20
```

<210> SEQ ID NO 5
<211> LENGTH: 20
<212> TYPE: DNA
<213> ORGANISM: Homo sapiens

<400> SEQUENCE: 5

```
gttttgttga ggatgttttt                                                 20
```

<210> SEQ ID NO 6
<211> LENGTH: 374
<212> TYPE: DNA
<213> ORGANISM: Artificial
<220> FEATURE:
<223> OTHER INFORMATION: sequence of 100% methylated PFN3 gene after
      bisulfite treatment

<400> SEQUENCE: 6

```
tttgtaaaga ttagttttt tatttataat ttttttttatc gcgtaagtgg aggaggagtt     60
agtcgcgttt aggttatagt ttatttggtt cgcgttatta gtgggcggtt tggttggtcg    120
gttaggcgtt ttgtatgcgt agttcgcgta tgagttcgtg tatcgttttg ttgaggatgt    180
ttttatgtac gtcgcgtcgg tttattagct attaggagcg cgcgcggcgt acggtttacg    240
tatacggcgc gcgcgtttag tttttttggtg cgtgcgttta gtacgtcgtt attttcggtt   300
agtaggtggt cgcggatgac gtagtagcgg cggtttttta cgtttaggtt cgtttgtagg    360
aaggtgtgtt tgtt                                                      374
```

<210> SEQ ID NO 7
<211> LENGTH: 215
<212> TYPE: DNA
<213> ORGANISM: Artificial
<220> FEATURE:
<223> OTHER INFORMATION: sequence of 100% methylated PFN3A locus after
      bisulfite treatment

<400> SEQUENCE: 7

```
gtgtatcgtt tgttgagga tgtttttatg tacgtcgcgt cggtttatta gtattaggag      60
cgcgcgcggc gtacggttta cgtatacggc gcgcgcgttt agttttttgg tgcgtgcgtt    120
tagtacgtcg ttattttcgg ttagtaggtg gtcgcggatg acgtagtagc ggcggttttt    180
tacgtttagg ttcgtttgta ggaaggtgtg tttgt                                215
```

<210> SEQ ID NO 8
<211> LENGTH: 53

```
<212> TYPE: DNA
<213> ORGANISM: Artificial
<220> FEATURE:
<223> OTHER INFORMATION: sequence of PFN3A locus analyzed by
      pyrosequencing
<220> FEATURE:
<221> NAME/KEY: misc_feature
<222> LOCATION: (1)..(53)
<223> OTHER INFORMATION: Y is T or C

<400> SEQUENCE: 8
atgtaygtyg ygtyggttta ttagtattag gagygygygy ggygtayggt tta          53
```